United States Patent
Ostersehlt et al.

[11] Patent Number: 5,214,047
[45] Date of Patent: May 25, 1993

[54] TETRACYCLIC QUINAZOLINE DERIVATIVES, EFFECTIVE AS ANTIARRYTHMIC AGENTS

[75] Inventors: Bernd Ostersehlt, Maxdorf; Rainer Schlecker, Bissersheim; Beatrice Rendenbach, Waldsee; Gerda von Philipsborn, Weinheim; Albrecht Franke, deceased, late of Wachenheim, all of Fed. Rep. of Germany, by Renate E. Franke, Catharina Franke, Tobias Franke, legal representatives

[73] Assignee: BASF Aktiengesellschaft, Ludwigshafen, Fed. Rep. of Germany

[21] Appl. No.: 243,469

[22] Filed: Sep. 12, 1988

[30] Foreign Application Priority Data

Sep. 12, 1987 [DE] Fed. Rep. of Germany ....... 3730718

[51] Int. Cl.$^5$ .................. A61K 31/505; C07D 487/14
[52] U.S. Cl. ..................... 514/257; 544/245; 544/247
[58] Field of Search ....................... 544/246, 245, 247; 514/257

[56] References Cited

U.S. PATENT DOCUMENTS

| | | | |
|---|---|---|---|
| 3,441,566 | 4/1969 | Houlihan | 544/252 |
| 3,743,733 | 7/1973 | Houlihan | 514/267 |
| 3,847,918 | 11/1974 | Kathawala | 544/247 |
| 3,887,566 | 6/1975 | Rodway et al. | 544/246 X |
| 4,058,529 | 11/1977 | Graf et al. | 544/246 X |

FOREIGN PATENT DOCUMENTS 2162590  7/1972  Fed. Rep. of Germany .
2082577  3/1982  United Kingdom .

*Primary Examiner*—Mukund J. Shah
*Assistant Examiner*—E. Bernhardt
*Attorney, Agent, or Firm*—Oblon, Spivak, McClelland, Maier & Neustadt

[57] ABSTRACT

A tetracyclic quinazoline derivative of the formula I:

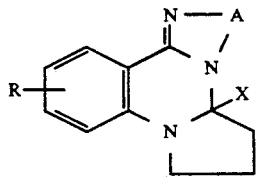

wherein A is $C_{2-3}$-alkylene or $C_{2-3}$-alkylene which is substituted by one or two $C_{1-4}$-alkyl radicals or A is cyclohexylene; X is phenyl, naphthyl or phenyl or naphthyl which is substituted by halogen, nitro, amino, $C_{1-4}$-alkylamino, sulfonylamino, $C_{1-4}$-acylamino, hydroxyl, $C_{1-4}$-alkoxy, —O—$(CH_2)_{2-4}$—$NR^1R^2$, $C_{1-4}$-alkyl or $C_{1-4}$-alkylsulfonyl, wherein $R^1$ and $R^2$ are each hydrogen or $C_{1-4}$-alkyl; or X is thienyl or thienyl which is substituted by chlorine, fluorine, methyl, ethyl, methoxy, ethoxy, nitro or hydroxyl; and R is hydrogen, halogen, nitro, amino, $C_{1-4}$-alkylamino, sulfonylamino, $C_{1-4}$-acylamino, hydroxyl, $C_{1-4}$-alkoxy, —O—$(CH_2)_{2-4}$—$NR^3R^4$, $C_{1-4}$-alkyl or $C_{1-4}$-alkylsulfonyl, wherein $R^3$ and $R^4$ are each hydrogen or $C_{1-4}$-alkyl, and the pharmaceutically acceptable salts thereof. The compounds and compositions of the present invention are effective as antiarrhythmic agents.

5 Claims, No Drawings

TETRACYCLIC QUINAZOLINE DERIVATIVES, EFFECTIVE AS ANTIARRYTHMIC AGENTS

The present invention relates to novel tetracyclic quinazoline derivatives which have valuable therapeutic, especially antiarrhythmic, properties, to a process for the preparation thereof, and to the use thereof for controlling diseases.

It is known that substituted quinazolines have hypotensive and bronchodilator properties (U.S. Pat. No. 3,441,566, German Laid-Open Application DOS 2,162,590).

We have now found that tetracyclic quinazoline derivatives of the formula I

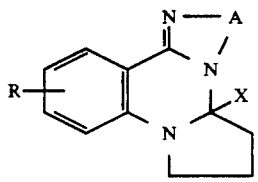

where A is $C_{2-4}$-alkylene which may be substituted by $C_{1-4}$-alkyl and in which 2 adjacent methylene groups may additionally be closed to a ring via a $C_3$-$C_5$-alkylene group which may be substituted by $C_{1-4}$-alkyl, X is a phenyl or naphthyl ring which may be substituted by halogen, nitro, amino, $C_{1-4}$-alkylamino, sulfonylamino, $C_{1-4}$-acylamino, hydroxyl, $C_{1-4}$-alkoxy, —O(CH$_2$)$_{2-4}$-NR$^1$R$^2$ (with R$^1$ and R$^2$ meaning hydrogen or $C_{1-4}$-alkyl), $C_{1-4}$-alkyl or $C_{1-4}$-alkylsulfonyl, or is a 5-membered heterocyclic ring which may be substituted, and R is hydrogen, halogen, nitro, amino, $C_{1-4}$-alkylamino, sulfonylamino, $C_{1-4}$-acylamino, hydroxyl, $C_{1-4}$-alkoxy, —O—(CH$_2$)$_{2-4}$-NR$^3$R$^4$ (with R$^3$ and R$^4$ meaning hydrogen or $C_{1-4}$-alkyl), $C_{1-4}$-alkyl or $C_{1-4}$-alkylsulfonyl, and the salts thereof with physiologically tolerated acids, surprisingly are class III antiarrhythmics. A in formula I is preferably $C_{2-3}$-alkylene which may be substituted by one or two $C_{1-4}$-alkyl radicals, and is especially $C_{2-3}$-alkylene which is substituted by one or two methyl radicals, X is preferably a phenyl or thienyl ring which is substituted by hydrogen, chlorine, fluorine, methyl, ethyl, methoxy, ethoxy, nitro or hydroxyl, and R is preferably ethoxy and especially hydrogen, fluorine, chlorine or methoxy.

The compounds of the formula I can be prepared by
a) reacting a compound of the formula II

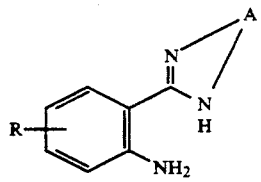

where A and R have the stated meanings, with an ω-halogeno ketone of the formula III

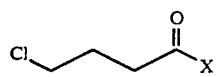

where X has the stated meaning, or b) reacting a compound of the formula IV

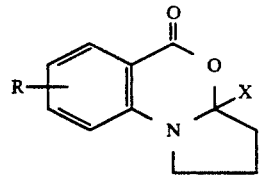

where R and X have the stated meanings, with a diamine of the formula V $$H_2N-A-NH_2 \qquad V$$

where A has the stated meaning, and possibly reacting the resulting compound of the formula I, if X is a phenyl or naphthyl which is substituted by hydroxyl, with an alkyl halide of the formula VI $$Hal—(CH_2)_{2-4}—NR^1R^2 \qquad VI$$

where Hal is halogen, and R$^1$ and R$^2$ have the stated meanings, or with a $C_{1-4}$-alkylsulfonyl chloride, and subsequently possibly converting the resulting compound into a salt thereof with a physiologically tolerated acid.

In the case of process a), the reactions are preferably carried out in the presence of a diluent or solvent, for example of a lower alcohol, and expediently at temperatures between 25° C. and the boiling point of the solvent used. The reactions are expediently carried out with the addition of a mineral acid, e.g. HCl, and possibly in the presence of catalytic amounts of NaI.

The preferred solvent for the reaction of the compounds II and III is ethanol, with the reaction preferably being carried out at the boiling point of the solvent. Completion of the reaction depends on the reactants and, in general, takes place within 8 to 60 hours. It is possible, in order to complete the reaction, to remove the solvent and to heat the residue at from 90° to 160° C., preferably at 110° to 130° C., expediently under an N$_2$ atmosphere, for 2 to 120 hours. The reaction product can be obtained in a conventional manner, e.g. by filtration, removal of the diluent or solvent from the reaction mixture by distillation, or extraction. The resulting compound is purified in a conventional manner, for example by recrystallization from a solvent or conversion into an acid addition compound.

Some of the starting compounds of the general formula II are known or can be prepared by methods known from the literature and as described, for example, in Houben-Weyl, Methoden der organischen Chemie (Methods of Organic Chemistry), Vol. 11/2, pages 38 et seq., G. Thieme Verlag, Stuttgart 1958, by reaction of an appropriate o-amino nitrile with a diamine of the general formula V, preferably with the addition of catalytic amounts of ammonium sulfide and sulfur.

The ω-halogeno ketones of the general formula III are known from the literature and can be prepared by Friedel-Crafts acylation of appropriately substituted aromatic compounds with ω-chlorobutyryl chloride by methods such as those described, for example, in Pharmazie 35, (1980), 140 or Industrie Chimique Belge, 9, (1960), 1073. Compounds of the general formula III are also obtained by nucleophilic ring opening of appropriately substituted cyclopropyl phenyl ketones with HCl by the method described in Journal of Labelled Compounds and Radiopharmaceuticals 21, (1984), 533.

The reaction of compounds of the general formula IV with a diamine V in process b) can be carried out at room temperature or higher temperatures, expediently at between 60° and 100° C. The starting compounds can be reacted in the presence of an inert, aprotic diluent or solvent. It is also possible to use the diamine V in excess as the diluent or solvent. Subsequently, to carry out the cyclization, after excess diamine and/or solvent has been removed the residue is heated in an inert high-boiling solvent, preferably tetralin, at from 150° to 220° C., expediently 180° to 200° C. The reaction product is obtained from the reaction mixture in a conventional manner by removing the solvent by distillation. Purification is in a conventional manner, for example by recrystallization from a solvent, by column chromatography or by conversion into an acid addition compound.

The starting compounds IV can be prepared as follows: an appropriately substituted o-aminobenzoic acid of the general formula VII

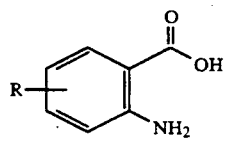

VII where R is as defined in the introduction, is reacted with an ω-halogeno ketone of the formula III in an inert solvent, e.g. benzene, toluene, xylene or chloro- or dichlorobenzene, expediently in the presence of catalytic amounts of acid, for example p-toluenesulfonic acid. The reaction is expediently carried out at the boiling point of the solvent used and with azeotropic removal of the water formed in the reaction. After the reaction is complete, it is possible to obtain the products in a conventional manner by removing the solvent by distillation and purify them by recrystallization from a suitabl solvent, preferably an alcohol having 1 to 4 C atoms.

Compounds of the formula I where A and R have the stated meanings and X is phenyl or naphthyl which, is substituted by one hydroxyl can be alkylated by known processes. For alkylation with the aminoalkyl halides VI, for example the anion is, initially formed from the hydroxyl compound with NaH in an inert aprotic solvent such as dimethylformamide, dimethylacetamide, dimethyl sulfoxide or dimethoxyethane, and is then reacted with the alkylating agent. The anion is formed at from 0° to 100° C., preferably from 20° to 50° C. The anion is reacted with the alkylating agent at from 0° to 80° C., preferably from room temperature to 50° C. The reaction with alkylsul-fonyl chlorides is carried out in inert aprotic solvents such as, for example, methylene chloride or chloroform with the addition of an acid-binding agent, preferably a tertiary amine, for example pyridine or triethylamine. The reaction can be carried out at from −20° C. to the boiling point of the solvent used, preferably from 0° to 60° C., especially at room temperature. The products are isolated and purified by conventional methods.

It is possible to convert the resulting compounds according to the invention into the acid addition salts thereof with physiologically tolerated acids. Examples of suitable conventional physiologically tolerated organic or inorganic acids are hydrochloric acid, hydrobromic acid, phosphoric acid, sulfuric acid, oxalic acid, maleic acid, fumaric acid, lactic acid, tartaric acid, adipic acid or benzoic acid. Others can be found in Fortschritte der Arzneimittelforschung, Vol. 10, pages 224 et seq., Birkhauser Verlag, Basel and Stuttgart, 1966.

The acid addition salts are, as a rule, obtained in a conventional manner by mixing the free base or solutions thereof with the appropriate acid or solutions thereof in an organic solvent, for example a lower alcohol such as methanol, ethanol or propanol, or an ether such as diethyl ether or methyl t-butylether. It is also possible, to improve deposition of crystals, to use mixtures of the said solvents. Furthermore, pharmaceutically acceptable aqueous solutions of acid addition compounds of the compounds I according to the invention can be prepared by dissolving the free bases in an aqueous acid solution.

The compounds of the formula I according to the invention have a center of chirality and are obtained as racemates which can be separated by conventional methods, for example by forming diastereomeric salts with optically active acids, into the optically active antipodes.

In some cases, the compounds of the formula I according to the invention have, depending on the choice of the amines V used, a second asymmetric carbon atom and can then be in the form of mixtures of diastereomers which can be separated in a conventional manner using physical/chemical methods into the pairs of diastereomers.

The novel compounds are antiarrhythmics. Vaughan Williams divides the latter into four groups, as follows:
I. Na channel inhibitors,
II. Adrenergic β-receptor blockers
III. K channel inhibitors and
IV. Ca antagonists The novel compounds are to be allocated to class III. As such, they are preferable to other antiarrhythmics in therapy, because they act on arrhythmias of various etiologies which are otherwise therapy-resistant. They abolish ventricular arrhythmias which occur after myocardial infarction and are based on a re-entry mechanism. In addition, they also act well on atrial dysrhythmias. Class III antiarrhythmics result in a prolongation of the QT interval in the ECG, without affecting the PQ interval and without markedly reducing the heart rate.

The action of the novel substances has been tested as follows:

The experimental animals used were male and female Pirbright white guinea pigs weighing 300–500 g. 1.5 g/kg urethane i.p. were used for anesthesia. The substances were administered intravenously. The extremity lead II was recorded to measure the ECG conduction times and the heart rate. The measured variables were the QT and PQ intervals and the heart rate. 4–6 animals were used for each dose. The criterion for a class III action was an increase in the QT interval compared with the values before administration of the substance. A PQ increase and a large decrease in the heart rate were used as exclusion criteria. The ED20% is calculated from the linear relation between log dose (mg/kg) of the substance and the relative prolongation of the QT interval (Δ%). The table shows the values obtained, together with the potency related to that of d-sotalol.

TABLE

| Substance of Example No. | Prolongation of the QT interval ED$_{20\%}$ mg/kg | Potency relative to to that of d-sotalol = 1.0 |
| --- | --- | --- |
| 1 | 1.0 | 3.6 |
| 2 | 1.1 | 3.3 |
| 4 | 0.21 | 17 |
| 5 | 1.0 | 3.5 |
| 7 | 0.86 | 4.3 |
| 8 | 0.61 | 6.0 |
| 9 | 1.5 | 2.4 |
| 11 | 0.40 | 9.0 |
| 13 | 0.99 | 3.7 |
| 15 | 0.43 | 8.5 |
| 19 | 1.4 | 2.6 |
| 21 | 0.46 | 8.0 |
| 22 | 0.56 | 6.5 |
| 24 | 0.29 | 12 |
| 25 | 0.58 | 6.2 |
| 26 | 1.5 | 2.4 |
| 27 | 0.42 | 8.7 |
| 28 | 0.94 | 3.9 |
| 29 | 0.55 | 6.6 |
| 30 | 1.0 | 3.6 |
| 31 | 0.56 | 6.5 |
| 33 | 1.5 | 2.4 |
| 34 | 0.61 | 6.0 |
| 35 | 0.63 | 5.7 |
| 37 | 0.69 | 5.3 |
| 38 | 0.83 | 4.4 |
| 41 | 0.46 | 7.8 |
| 42 | 0.78 | 4.7 |
| 43 | 0.60 | 6.1 |
| 44 | 0.49 | 7.4 |
| 45 | 0.59 | 6.2 |
| 46 | 0.55 | 6.7 |
| 47 | 0.52 | 7.0 |
| 48 | 0.31 | 11.8 |
| 49 | 0.32 | 11 |
| 50 | 0.25 | 15 |
| 53 | 1.0 | 3.6 |
| d-sotalol | 3.6 | 1.0 |

The table shows that in terms of QT prolongation the substances according to the invention are 2.4 to 17 times as effective as the known class III antiarrhythmic d-sotalol.

The compounds according to the invention can be administered orally or parenterally (subcutaneously, intravenously, intramuscularly or intraperitoneally) in a conventional manner. Administration can also take place with vapors or sprays through the nasopharyngeal space.

The dosage depends on the age, condition and weight of the patient and on the mode of administration. As a rule, the daily dose of active compound is from about 10 to 500 mg per patient and day on oral administration and from about 1 to 50 mg per patient and day on parenteral administration.

The novel compounds can be used in conventional solid or liquid pharmaceutical administration forms, e.g. as tablets, film-coated tablets, capsules, powders, granules, sugar-coated tablets, suppositories, solutions or sprays. These are prepared in a conventional manner. It is possible in this connection for the active compounds to be processed with the customary pharmaceutical auxiliaries such as tablet binders, fillers, preservatives, tablet disintegrants, flow regulators, plasticizers, wetting agents, dispersing agents, emulsifiers, solvents, retardants, antioxidants and/or propellant gases (cf. H. Sucker et al.: Pharmazeutische Technologie (Pharmaceutical Technology), Thieme Verlag, Stuttgart, 1978). The administration forms obtained in this way normally contain from 1 to 99% by weight of the active compound.

The Examples which follow are intended to explain the invention in detail.

EXAMPLE 1

2,3,5,6,7,8-Hexahydro-5-(4-methylphenyl)imidazo[1,2-c]pyrrolo[1,2-a]quinazoline

A mixture of 10.2 g of 4-chloro-1-(4-methylphenyl)-1-butanone, 8.1 g of 2-(2-aminophenyl)-4,5-dihydroimidazole, 0.5 g of sodium iodide and 250 ml of ethanol at room temperature was mixed with 5.5 ml of 12 N HCl and then refluxed for 30 h. The solvent was removed, and the residue was heated at 120° C. under an N$_2$ atmosphere for 4 h. After cooling, the residue was partitioned in H$_2$O/methyl t-butyl ether, and the insoluble constituents were removed by filtration with suction. The phases were separated, and the aqueous phase was basified with 5 N sodium hydroxide solution, resulting in the formation of a yellow-brown substance in the form of an oil, which was extracted by shaking three times with methylene chloride. The solution was dried with MgSO$_4$ and then filtered, the solvent was removed by distillation, and the crude product (13.1 g) was dissolved in hot ethyl acetate. The product separated out in the form of colorless crystals on cooling.

Yield: 10.8 g (71%), melting point 187°–189° C.;

| C$_{20}$H$_{21}$N$_3$ (303.4) | calc. | C 79.17 | H 6.98 | N 13.85 |
| --- | --- | --- | --- | --- |
| | found | C 78.9 | H 7.1 | N 13.8 |

The following were prepared in analogy to Example 1:
2.  5-(4-Chlorophenyl)-2,3,5,6,7,8-hexahydroimidazo[1,2-c]pyrrolo[1,2-a]quinazoline
Yield: 7.2 g (36%), melting point 158°–160° C. (ethanol)
3.  12-Chloro-2,3,5,6,7,8-hexahydro-5-phenylimidazo[1,2-c]pyrrolo[1,2-a]quinazoline
Yield: 8.9 g (54%), melting point 249°–250° C. (ethanol)
4.  5-(4-Fluorophenyl)-2,3,5,6,7,8-hexahydroimidazo[1,2-c]pyrrolo[1,2-a]quinazoline
Yield: 10.5 g (68%), melting point 177° C. (decomposition)
5.  2,3,5,6,7,8-Hexahydro-11,12-dimethoxy-5-phenylimidazo[1,2-c]pyrrolo[1,2-a]quinazoline
Yield: 4.8 g (51%), melting point 171° C. (ethanol)
6.  2,3,5,6,7,8-Hexahydro-11,12-dimethoxy-5-(3,4-dimethoxyphenyl)imidazo[1,2-c]pyrrolo[1,2-a]quinazoline hydrochloride
Yield: 4.5 g (62%), melting point 221° C. (decomposition) (isopropanol)
7.  2,3,5,6,7,8-Hexahydro-5-(4-hydroxyphenyl)imidazo[1,2-c]pyrrolo[1,2-a]quinazoline hydrochloride
Yield: 25.3 g (74%), melting point 275°–277° C. (decomposition) (methanol/ethanol)
8.  2,3,5,6,7,8-Hexahydro-5-(4-methoxyphenyl)imidazo[1,2-c]pyrrolo[1,2-a]quinazoline
Yield: 7.7 g (48%), melting point 110°–112° C.
9.  5-(3,4-Dichlorophenyl)-2,3,5,6,7,8-hexahydroimidazo[1,2-c]pyrrolo[1,2-a]quinazoline
Yield: 4.4 g (71%), melting point 218°–222° C.
10.  2,3,5,6,7,8-Hexahydro-5-(2,4-dimethylphenyl)imidazo[1,2-c]pyrrolo[1,2-a]quinazoline Yield: 5.0 g (32%), melting point 175°–180° C. (decomposition)
11. 11-Chloro-2,3,5,6,7,8-hexahydro-5-phenylimidazo[1,2-c]pyrrolo[1,2-a]quinazoline
Yield: 10.0 g (62%), melting point 177°–181° C.
12. 2,3,5,6,7,8-Hexahydro-5-(2-thienyl)imidazo[1,2-c]pyrrolo[1,2-a]quinazoline
Yield: 7.5 g (51%), melting point 159°–161° C.
13. 5-(2,4-Dichlorophenyl)-2,3,5,6,7,8-hexahydroimidazo[1,2-c]pyrrolo[1,2-a]quinazoline hydrochloride
Yield: 10.1 g (51%), melting point 200° C. (decomposition) (ethanol/methyl t-butyl ether)
14. 5-(4-Bromophenyl)-2,3,5,6,7,8-hexahydroimidazo[1,2-c]pyrrolo[1,2-a]quinazoline hydrochloride
Yield: 8.2 g (52%), melting point 273°–274° C. (ethanol/methyl t-butyl ether)
15. 11-Chloro-5-(4-fluorophenyl)-2,3,5,6,7,8-hexahydroimidazo[1,2-c]pyrrolo[1,2-a]quinazoline hydrochloride
Yield: 16.9 g (82%), melting point 240°–243° C. (ethanol/methyl t-butyl ether)
16. 5-(4-Aminophenyl)-2,3,5,6,7,8-hexahydroimidazo[1,2-c]pyrrolo[1,2-a]quinazoline hydrochloride
Yield: 3.9 g (32%), melting point 259°–261° C. (ethanol/diethyl ether)
17. 2,3,5,6,7,8-Hexahydro-5-(α-naphthyl)imidazo[1,2-c]pyrrolo[1,2-a]quinazoline
Yield: 6.4 g (61%), melting point 216°–217° C. (decomposition)
18. 2,3,5,6,7,8-Hexahydro-5-(3-nitrophenyl)imidazo[1,2-c]pyrrolo[1,2-a]quinazoline hydrochloride
Yield: 8.0 g (86%), melting point 297°–298° C. (ethanol/methyl t-butyl ether)
19. 5-(2-(5-Chlorothienyl))-2,3,5,6,7,8-hexahydroimidazo[1,2-c]pyrrolo[1,2-a]quinazoline hydrochloride
Yield: 13.4 g (73%), melting point 245°–248° C. (ethanol/diethyl ether)
20. 2,3,5,6,7,8-Hexahydro-5-(4-methylsulfonylaminophenyl)imidazo[1,2-c]pyrrolo[1,2-a]quinazoline hydrochloride
Yield: 8.4 g (59%), melting point 296°–297° C. (methanol)
21. 2,3,5,6,7,8-Hexahydro-5-(4-nitrophenyl)imidazo[1,2-c]pyrrolo[1,2-a]quinazoline hydrochloride
Yield: 1.5 g (51%), melting point 295° C. (decomposition) (ethanol)
22. 2,3,5,6,7,8-Hexahydro-2,3-tetramethylene-5-phenylimidazo[1,2-c]pyrrolo[1,2-a]quinazoline
Yield: 3.9 g (51%), melting point 168°–170° C.
23. 2,3,5,6,7,8-Hexahydro-5-(4-fluorophenyl)-2,3-tetramethyleneimidazo[1,2-c]pyrrolo[1,2-a]quinazoline hydrochloride
Yield: 5.7 g (67%), melting point 160° C. (decomposition) (ethanol)
24. 2,3,5,6,7,8-Hexahydro-3-methyl-5-phenylimidazo[1,2-c]pyrrolo[1,2-a]quinazoline hydrochloride
Yield: 2.8 g (29%), melting point 238°–240° C. (ethanol/methyl t-butyl ether)
25. 2,3,6,7,8,9-Hexahydro-6-(2-thienyl)-2H-pyrimido[1,2-c]pyrrolo[1,2-a]quinazoline
Yield: 5.2 g (34%), melting point 136°–138° C.
26. 6-(4-Chlorophenyl)-2,3,6,7,8,9-hexahydro-2H-pyrimido[1,2-c]pyrrolo[1,2-a]quinazoline
Yield: 10.3 g (61%), melting point 148°–150° C.
27. 6-(4-Fluorophenyl)-2,3,5,6,7,8-hexahydro-2H-pyrimido[1,2-c]pyrrolo[1,2-a]quinazoline
Yield: 9.1 g (57%), melting point 154°–156° C.
28. 6-(3,4-Dichlorophenyl)-2,3,5,6,7,8-hexahydro-2H-pyrimido[1,2-c]pyrrolo[1,2-a]quinazoline
Yield: 3.5 g (51%), melting point 155°–157° C.
29. 13-Chloro-2,3,5,6,7,8-hexahydro-6-phenyl-2H-pyrimido[1,2-c]pyrrolo[1,2-a]quinazoline hydrochloride
Yield: 4.5 g (24%), melting point 320° C. (decomposition) (ethanol/methyl t-butyl ether)
30. 13-Chloro-6-(4-fluorophenyl)-2,3,5,6,7,8-hexahydro-2H-pyrimido[1,2-c]pyrrolo[1,2-a]quinazoline
Yield: 9.3 g (53%), melting point 197°–201° C.
31. 2,3,5,6,7,8-Hexahydro-6-(3-nitrophenyl)-2H-pyrimido[1,2-c]pyrrolo[1,2-a]quinazoline
Yield: 7.5 g (47%), melting point 141°–143° C.
32. 2,3,5,6,7,8-Hexahydro-6-(4-methylsulfonylaminophenyl)-2H-pyrimido[1,2-c]pyrrolo[1,2-a]quinazoline hydrochloride
Yield: 5.6 g (41%), melting point 175°–177° C. (decomposition) (acetone/water)
33. 6-(2-(5-Chlorothienyl))-2,3,5,6,7,8-hexahydro-2H-pyrimido[1,2-c]pyrrolo[1,2-a]quinazoline
Yield: 5.6 g (33%), melting point 245° C. (decomposition) (ethanol/diethyl ether)
34. 2,3,5,6,7,8-Hexahydro-6-(4-nitrophenyl)-2H-pyrimido[1,2-c]pyrrolo[1,2-a]quinazoline
Yield: 9.6 g (61%), melting point 287° C. (decomposition) (methanol)
35. 2,3,5,6,7,8-Hexahydro-6-(4-methoxyphenyl)-2H-pyrimido[1,2-c]pyrrolo[1,2-a]quinazoline hydrochloride
Yield: 4.1 g (22%), melting point 247° C. (ethanol/methyl t-butyl ether)
36. 6-(2,4-Dichlorophenyl)-2,3,5,6,7,8-hexahydro-2H-pyrimido[1,2-c]pyrrolo[1,2-a]quinazoline fumarate
Yield: 6.0 g (40%), melting point 207°–209° C. (decomposition) (ethanol/methyl t-butyl ether)
37. 12-Chloro-2,3,5,6,7,8-hexahydro-6-phenyl-2H-pyrimido[1,2-c]pyrrolo[1,2-a]quinazoline hydrochloride
Yield: 10.8 g (58%), melting point 289°–292° C. (ethanol)
38. 2-Chloro-6-(4-fluorophenyl)-2,3,5,6,7,8-hexahydro-2H-pyrimido[1,2-c]pyrrolo[1,2-a]quinazoline hydrochloride
Yield: 6.9 g (35%), melting point 271°–273° C. (ethanol)
39. 2,3,5,6,7,8-Hexahydro-6-(4-hydroxyphenyl)-2H-pyrimido[1,2-c]pyrrolo[1,2-a]quinazoline hydrochloride
Yield: 11.0 g (62%), melting point 150° C. (decomposition) (ethanol)
40. 6-(4-Bromophenyl)-2,3,5,6,7,8-hexahydro-2H-pyrimido[1,2-c]pyrrolo[1,2-a]quinazoline hydrochloride
Yield: 7.0 g (43%), melting point 298°–302° C. (decomposition) (ethanol/methyl t-butyl ether)
41. 2,3,5,6,7,8-Hexahydro-3,3-dimethyl-6-phenyl-2H-pyrimido[1,2-c]pyrrolo[1,2-a]quinazoline hydrochloride
Yield: 8.9 g (49%), melting point 304°–306° C. (ethanol)
42. 2,3,5,6,7,8-Hexahydro-3,3-dimethyl-6-(4-nitrophenyl)-2H-pyrimido[1,2-c]pyrrolo[1,2-a]quinazoline hydrochloride Yield: 2.6 g (63%), melting point 326° C. (ethanol)

43. 2,3,5,6,7,8-Hexahydro-3,3-dimethyl-5-phenylimidazo[1,2-c]pyrrolo[1,2-a]quinazoline hydrochloride Yield: 15.0 g (80%), melting point 269° C. (ethanol)

44. 2,3,5,6,7,8-Hexahydro-4,4-dimethyl-6-phenyl-2H-pyrimido[1,2-c]pyrrolo[1,2-a]quinazoline hydrochloride Yield: 6.5 g (72%), melting point 287° C. (ethanol/methyl t-butyl ether)

45. 5-(4-Fluorophenyl)-2,3,5,6,7,8-hexahydro-3,3-dimethylimidazo[1,2-c]pyrrolo[1,2-a]quinazoline hydrochloride Yield: 3.9 g (35%), melting point 251° C. (ethanol)

46. 2,3,5,6,7,8-Hexahydro-3,3-dimethyl-5-(4-nitrophenyl)imidazo[1,2-c]pyrrolo[1,2-a]quinazoline hydrochloride Yield: 5.3 g (46%), melting point >300° C. (ethanol)

47. 2,3,5,6,7,8-Hexahydro-4,4-dimethyl-6-(4-nitrophenyl)-2H-pyrimido[1,2-c]pyrrolo[1,2-a]quinazoline hydrochloride Yield: 5.0 g (47%), melting point >300° C. (ethanol)

48. 2,3,5,6,7,8-Hexahydro-3-methyl-5-(4-nitrophenyl)imidazo[1,2-c]pyrrolo[1,2-a]quinazoline hydrochloride Yield: 5.1 g (46%), melting point 283°-285° C. (ethanol)

EXAMPLE 49

2,3,5,6,7,8-Hexahydro-6-phenyl-2H-pyrimido[1,2-c]pyrrolo[1,2-a]quinazoline hydrochloride a)

1,2,3,3a-Tetrahydro-3a-phenyl-5H-pyrrolo[1,2-a]-3,1-benzoxazin-5-one (Formula IV, $R^3$=H, X=$C_6H_5$)

A mixture of 26.1 g of 2-aminobenzoic acid, 36.5 g of 4-chloro-1-phenyl-1-butanone, 0.5 g of p-toluenesulfonic acid and 250 ml of xylene were refluxed with a water trap. After the reaction was complete, the solvent was removed by distillation and the remaining solid was recrystallized from ethanol. Yield: 41.1 g (81.5%), melting point 152° C.

b)

2,3,5,6,7,8-Hexahydro-6-phenyl-2H-pyrimido[1,2-c]pyrrolo[1,2-a]quinazoline hydrochloride 6.2 g of 1,2,3,3a-tetrahydro-3a-phenyl-5H-pyrrolo[1,2-a]-3,1-benzoxazin-5-one were dissolved in 15 ml of 1,3-diaminopropane and stirred at 80° C. for 3 h. Then 35 ml of tetralin were added to this solution, the internal temperature was increased to 190° C. within 30 min, and the excess diamine was removed by distillation. After 6 h, the mixture was concentrated at 190° C. under reduced pressure, and the residue was allowed to cool to about 70° C. and was dissolved in 15 ml of ethanol. The crude product which slowly crystallized out after addition of 8 ml of 3N ethereal HCl was filtered off with suction and washed with a little ethanol.

Yield: 4.4 g (55.5%), melting point 285°-286° C.

The following was prepared in analogy to Example 49:

50. 2,3,5,6,7,8-Hexahydro-5-phenylimidazo[1,2-c]pyrrolo[1,2-a]quinazoline hydrochloride Yield: 3.6 g (45%); melting point 308°-310° C.

EXAMPLE 51

2,3,5,6,7,8-Hexahydro-5-(4-(2-dimethylaminoethoxy)phenyl)imidazo[1,2-c]pyrrolo[1,2-a]quinazoline hydrochloride 5 g of 2,3,5,6,7,8-hexahydro-5-(4-hydroxyphenyl)imidazo[1,2-c]pyrrolo[1,2-a]quinazoline hydrochloride (Example 7) suspended in 200 ml of dimethylformamide were slowly added at room temperature to a suspension of 1.5 g of sodium hydride in 100 ml dimethylformamide. After evolution of gas was complete, 3 g of 2-chloroethyldimethylamine were added, and the mixture was stirred at room temperature for 20 h. The reaction solution was mixed with $H_2O$ and extracted with methylene chloride. The organic phase was washed with $H_2O$, dried over magnesium sulfate and concentrated. The remaining oily residue was taken up in a little isopropanol, 4.5 ml of 3 N ethereal HCl were added, and the solid which separated out was recrystallized from ethanol/methyl t-butyl ether. Yield: 2.0 g (33%); melting point 304° C. (decomposition).

The following was prepared by a similar method:

52. 2,3,5,6,7,8-Hexahydro-5-(4-(2-pyrrolidinoethoxy)phenyl)imidazo[1,2-c]pyrrolo[1,2-a]quinazoline dihydrochloride Yield: 6.1 g (43%); melting point 289° C. (methanol/methyl t-butyl ether)

53. 2,3,5,6,7,8-Hexahydro-5-(4-methylsulfonyloxyphenyl)imidazo[1,2-c]pyrrolo[1,2-a]quinazoline hydrochloride 6 ml of methylsulfonyl chloride were added dropwise at 0°-5° C. to a vigorously stirred suspension of 8.55 g of 2,3,5,6,7,8-hexahydro-5-(4-hydroxyphenyl)imidazo[1,2-c]pyrrolo[1,2-a]quinazoline hydrochloride in 100 ml of methylene chloride and 25 ml of pyridine, and the reaction mixture was stirred at room temperature for 70 h. The solvent was removed by distillation and then 1N HCl was added, and the resulting precipitate was recrystallized from ethanol/methyl t-butyl ether. Yield: 8.0 g (76%); melting point 241°-242° C. (decomposition).

Examples of pharmaceutical administration forms:

A) Tablets of the following composition are compressed in a tabletting press in a conventional manner:
- 40 mg of substance of Example 28
- 120 mg of corn starch
- 13.5 mg of gelatin
- 45 mg of lactose
- 2.25 mg of Aerosil ® (chemically pure silica in submicroscopically fine distribution)
- 6.75 mg of potato starch (as 6% paste)

B) Sugar-coated tablets of the following composition are prepared in a conventional manner:
- 20 mg of substance of Example 42
- 60 mg of core composition
- 60 mg of sugar-coating composition The core composition consists of 9 parts of corn starch, 3 parts of lactose and 1 part of Luviskol ® VA 64 (60:40 copolymer of vinylpyrrolidone/vinyl acetate, cf. Pharm. Ind. 1962, 586). The sugar-coating composition consists of 5 parts of sucrose, 2 parts of corn starch, 2 parts of calcium carbonate and 1 part of talc. The sugar-coated tablets prepared in this way are then provided with an enteric coating.

C) 10 g of substance of Example 41 are dissolved in 5000 ml of water with the addition of NaCl, and the pH is adjusted to 6.0 with 0.1N NaOH so that a solution which is isotonic with blood is produced. 1 ml portions of this solution are dispensed into ampoules and sterilized.

We claim:

1. A tetracyclic quinazoline derivative of the formula I:

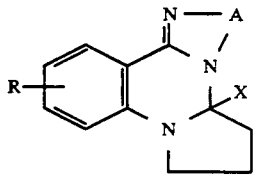

wherein A is $C_{2-3}$-alkylene or $C_{2-3}$-alkylene which is substituted by one or two $C_{1-4}$-alkyl radicals or A is cyclohexylene; X is phenyl, naphthyl or phenyl or naphthyl which is substituted by halogen, nitro, amino, $C_{1-4}$-alkylamino, sulfonylamino, $C_{1-4}$-acylamino, hydroxyl, $C_{1-4}$-alkoxy, $-O-(CH_2)_{2-4}-NR^1R^2$, $C_{1-4}$-alkyl or $C_{1-4}$-alkylsulfonyl, wherein $R^1$ and $R^2$ are each hydrogen or $C_{1-4}$-alkyl; or X is thienyl or thienyl which is substituted by chlorine, fluorine, methyl, ethyl, methoxy, ethoxy, nitro or hydroxyl; and R is hydrogen, halogen, nitro, amino, $C_{1-4}$-alkylamino, sulfonylamino, $C_{1-4}$-acylamino, hydroxyl, $C_{1-4}$-alkoxy, $-O-(CH_2)_{2-4}-NR^3R^4$, $C_{1-4}$-alkyl or $C_{1-4}$-alkylsulfonyl, wherein $R^3$ and $R^4$ are each hydrogen or $C_{1-4}$-alkyl, and the pharmaceutically acceptable salts thereof.

2. The tetracyclic quinazoline derivative as claimed in claim 1, wherein A is $C_{2-3}$-alkylene or $C_{2-3}$-alkylene which is substituted by one or two $C_{1-4}$-alkyl radicals; X is phenyl or thienyl which is substituted by chlorine, fluorine, methyl, ethyl, methoxy, ethoxy, nitro or hydroxyl; and R is hydrogen, fluorine, chlorine, methoxy or ethoxy.

3. The tetracyclic quinazoline derivative as claimed in claim 2, wherein A is $C_{2-3}$-alkylene which is substituted by one or two methyl radicals.

4. A therapeutic composition, comprising an effective amount of a compound of claim 1 as an active ingredient, and a pharmaceutically acceptable carrier.

5. A method of treating atrial and ventricular dysrhythmias in a patient suffering therefrom, which comprises administering an effective amount of a compound of claim 1 to said patient.